United States Patent
Hale et al.

(10) Patent No.: US 7,101,968 B2
(45) Date of Patent: Sep. 5, 2006

(54) ONE-STEP REDUCTION AND ALKYLATION OF PROTEINS

(75) Inventors: John Hale, Fishers, IN (US); Michael Knierman, Indianapolis, IN (US)

(73) Assignee: Indiana Proteomics Consortium LLC, Indianapolis, IN (US)

( * ) Notice: Subject to any disclaimer, the term of this patent is extended or adjusted under 35 U.S.C. 154(b) by 170 days.

(21) Appl. No.: 10/654,062

(22) Filed: Sep. 3, 2003

(65) Prior Publication Data

US 2004/0176579 A1    Sep. 9, 2004

(51) Int. Cl.
*C07K 1/00*    (2006.01)
(52) U.S. Cl. .................................... 530/345
(58) Field of Classification Search ............... 530/408, 530/345
See application file for complete search history.

(56) References Cited

OTHER PUBLICATIONS

Hampton Research TCEP HC User Guide*
Laing, P., et al, Journal of Biological Chemistry (1997), vol. 272, pp. 19051-19058.*
Hale, J.E. et al, Amino Acids (1996), vol. 10, pp. 243-252.*
Getz, E.B., Analytical Biochemistry (1999), vol. 273, pp. 73-80.*
http://www.webster.com/cgi-bin/dictionary?book=Dictionary&va=reagent.*
Hale et al., "Analysis of Cysteine Residues in Peptides and Proteins Alkylated with Volatile Reagents", *Amino Acids*, 1996, vol. 10, pp. 243-252.
Galvani et al., "Alkylation Kinetics of Proteins in Prepration for Two-Dimensional Maps: A Matrix Assisted Laser Desorption/Ionization-Mass Spectrometry Investigation", *Electrophoresis*, 2001, vol. 22, pp. 2058-2068.
Taniuchi et al., "The Amino Acid Sequence of an Extracellular Nuclease of *Staphylococcus Aureus*", *The Journal of Biological Chemistry*, vol. 241, No. 19, Oct. 10, 1966, pp. 4366-4385.
Herbert et al., "Reduction and Alkylation of Proteins in Preparation of Two-Dimensional Map Analysis: Why, When, and How?", *Electrophoresis*, 2001, vol. 22, pp. 2046-2057.
"In-Gel Digest of Silver Strained Proteins Destain and Reduction/Alkylation Protocols", *Millipore*, 2002, 1 page.
"Estimation of the Disulfide Content of Trypsin Inhibitors as S-β-(2-Pyrideylethyl)-L-cysteine" by Friedman et al.; 1980: Analytical Biochemistry. vol. 106; pp. 27-34.
"Peptide Mapping of Complex Proteins at the Low-Picomole Level with Capillary Electrophoretic Separations," by Cobb et al.; 1992; Analytical Chemistry, vol. 64, No. 8, pp. 879-886.
"On-Line Procedures for Alkylation of Cysteine Residues with 3-Bromopropylamine prior to Protein Sequence Analysis," by Jue et al.; 1994; Analytical Chemistry, vol. 221, No. 2, pp. 374-378.

* cited by examiner

*Primary Examiner*—Bruce R. Campell
*Assistant Examiner*—Thomas S. Heard
(74) *Attorney, Agent, or Firm*—Bose McKinney & Evans LLP (57) ABSTRACT

The present invention relates generally to the field of analyzing proteins and more specifically to the reduction and alkylation of protein samples during protein analysis. A novel composition and method for reducing and alkylating proteins is disclosed. A novel reagent including a combination of a volatile reducing agent, a volatile alkylating agent, and a volatile solvent is used for a one-step reduction and alkylation of proteins allowing the protein sample to remain in the same container during the reduction and alkylation processes.

45 Claims, 10 Drawing Sheets

ONE-STEP REDUCTION AND ALKYLATION OF PROTEINS

FIELD OF INVENTION

The invention relates generally to the field of analyzing proteins and more specifically to the reduction and alkylation of protein samples during protein analysis.

BACKGROUND AND SUMMARY

Many proteins such as lysozyme are formed from folded polypeptides which are held in place by disulfide bonds that link the folds. Analysis of proteins often involve restriction or cutting apart of the polypeptides by enzymes, such as trypsin, at specific locations of the protein. After the protein has been cut apart, specific sites on the protein can be studied. Sometimes, the specific locations where the enzyme is to cut apart the protein is inaccessible to the enzyme because of the folding.

One method for unfolding the polypeptides is to reduce the disulfide bond linking the folded polypeptides. Reduction is accomplished by adding a reducing agent to the protein. After the proteins have been reduced, typically they are alkylated to avoid reforming of the disulfide bonds. An alkylating agent is added to the protein to alkylate it. The protein is then prepared for restriction or cutting apart of the polypeptides by enzymes. Usually the reduction step involves incubating the protein sample at a specified temperature followed by multiple washings or desalting steps. After the washings, the alkylation step is carried out and also usually involves incubation followed by multiple washings or desalting.

Common prior art reducing agents used to reduce proteins include dithiothrediol (DTT) and tricarboxyethylphosphene, neither of which are volatile under a partial vacuum at around room temperature. One method of reducing a protein involves incubating the protein with one of a reducing agent followed by three washing steps. After the reducing step, the protein is then incubated with an alkylating agent such as iodoacetamide or iodoacetic acid, after which the sample is then again subjected to multiple washing steps. Lodoacetamide and iodoacetic acid are also not volatile under a partial vacuum at about room temperature. Although the method for reducing and alkylating proteins described above is common, it is tedious, time consuming, and provides multiple opportunities to lose all or a portion of the protein sample, especially when small samples are involved. The present invention is directed to decrease the amount of time involved in the reduction and alkylation of protein samples and reduce the risk of losing all or a portion of the protein sample.

One embodiment of the present invention includes a composition configured to modify proteins, the composition comprising a single volatile reagent. Another embodiment of the present invention includes a method of modifying proteins comprising the steps of providing a volatile reagent configured to reduce and alkylate the proteins, the reagent including a sufficient amount of solvent to substantially dissolve the proteins, and dissolving the proteins in the volatile reagent. Another embodiment of the present invention includes a kit for one-step reduction and alkylation of a protein sample, the kit including a volatile reducing agent configured to reduce the protein sample, a volatile alkylating agent configured to alkylate the protein sample, and a volatile solvent configured to substantially dissolve the protein sample.

DETAILED DESCRIPTION

The present invention relates to a composition and method for reducing and alkylating proteins such as lysozyme. The composition to reduce and alkylate the proteins is a reagent including a combination of a reducing agent, an alkylating agent, and a solvent to dissolve the particular protein. The reducing agent, the alkylating agent, and the solvent are selected from materials that are volatile under a partial vacuum. The reducing agent, the alkylating agent and the solvent can each be an individual material or a combination of such materials. For example, it may be possible for a single composition to reduce, alkylate and dissolve the protein.

The reducing agent may include any reducing agent or combination or reducing agents that are volatile under a partial vacuum. Reducing agents include triethylphosphine and trimethylphosphene or any other suitable reducing agent that is volatile when subjected to a partial vacuum. Selection of the volatile reducing agent will depend upon its ability to substantially reduce the protein being treated.

The alkylating agent of the reagent can include any alkylating agent or combination of alkylating agents that are volatile under a partial vacuum. Lodoethanol and bromoethanol are examples of suitable alkylating agents. Any suitable alkylating agent that is volatile when subjected to a partial vacuum could be used. The selected volatile alkylating agent must be able to adequately alkylate the protein sample.

Generally, the reagent includes a reducing agent, an alkylating agent, and a solvent, all of which are volatile. The solvent is selected to dissolve the protein sample. Experimental results have shown that the solvent may be up to 100% organic solvent, although in the preferred embodiment it is about 50% water, 50% organic solvent. A suitable solvent is acetonitrile, although one having skill in the art would understand that other volatile organic solvents, or mixture of solvents could be used. Aqueous mixtures of organic solvents may also be used. Aqueous mixtures of acetonitrile have been used with good results, especially in connection with dyed proteins held in gels where it was observed to effectively remove the dye from the immobilized protein.

The one-step method of reducing and alkylating a protein sample utilizing the reagent first involves the step of selecting suitable volatile reducing and alkylating agents and a suitable volatile solvent, if needed, to dissolve the protein sample. To create the reagent, the selected reducing agent, alkylating agent, and solvent are combined in a single container such as a test tube. Next, the protein sample is placed in the container with the reagent after which the reagent and the protein sample are incubated at a specified temperature for a specified time period to promote the reduction and alkylation processes. The incubated mixture is then subjected to a partial vacuum to remove the unreacted portion of the reagent, leaving a dried, reduced and alkylated protein sample suitable for rehydration and further treatment, such as by enzymes. It should be noted that the components of the reagent could be added to the protein sample simultaneously as described above or sequentially. This one-step method of reducing and alkylating a protein sample can also be used for gas phase reactions.

In an alternative embodiment, the solvent and the reducing agent are mixed together to produce a first mixture before mixing with the protein sample. The first mixture is then mixed with the protein sample to produce a second mixture. The alkylating agent is then mixed with the second mixture. In another embodiment, the second mixture is incubated and the solvent and the reducing agent are subsequently removed by heat, vacuum, or any other suitable method after which a mixture containing solvent and the alkylating agent is added to the dried protein sample.

In the preferred embodiment, the incubation step is carried out at 37° C. for about one hour. Alternatively, the reaction can be conducted at room temperature (about 23° C.). In the preferred embodiment, this one-step reduction alkylation process is carried out at elevated temperatures to reduce the time of the reaction such that it is practical for normal laboratory use. The speed of the reduction and alkylation reactions can be increased by buffering the reagent to a high pH, preferably a pH of about 10. The buffer used in the preferred embodiment of the present invention is 0.1M ammonium carbonate, although any suitable buffer may be used.

Following the incubation step, the remaining volatile components of the reagent are removed under a vacuum of about $10^{-2}$ mTorr for about an hour, leaving a dried protein material or a dried gel containing the immobilized protein, depending upon the starting material. The protein can then be easily resolubulized in any enzyme containing solution for further processing.

Any trace amounts of the reducing agent, alkylating agent, or the solvent that remain in the reduced and alkylated protein sample can be neutralized by the addition of small amounts of a chelated metal, such as copper (II) citrate, to the material used to resolubulize the protein. Any other suitable chelated metal may also be used.

The composition and method of the present invention can be used to treat proteins from any common source such as isolated or fractionated protein supplied on a gel or, for example, a mixture of proteins found in a serum. Although the step of removing the remaining volatile components of the reagent by subjecting the protein/reagent solution to a partial vacuum is described in the preferred embodiment, this step is not necessary. In an alternative embodiment, following the incubation step, the protein/reagent solution can be air dried by simply allowing the solution to be exposed to room temperature air for a period of one to four hours to allow the remaining volatile components to evaporate leaving the dried protein material.

In another alternative embodiment, the remaining volatile components can be removed by heating the protein/reagent solution to evaporate the volatile components. In yet another alternative embodiment, a stream of compressed nitrogen can be applied to the incubated protein/reagent solution to remove the volatile components. Any suitable method for removing the volatile components remaining after the protein/reagent solution has been incubated could be used in the one-step alkylation/reduction method.

Figure 1:
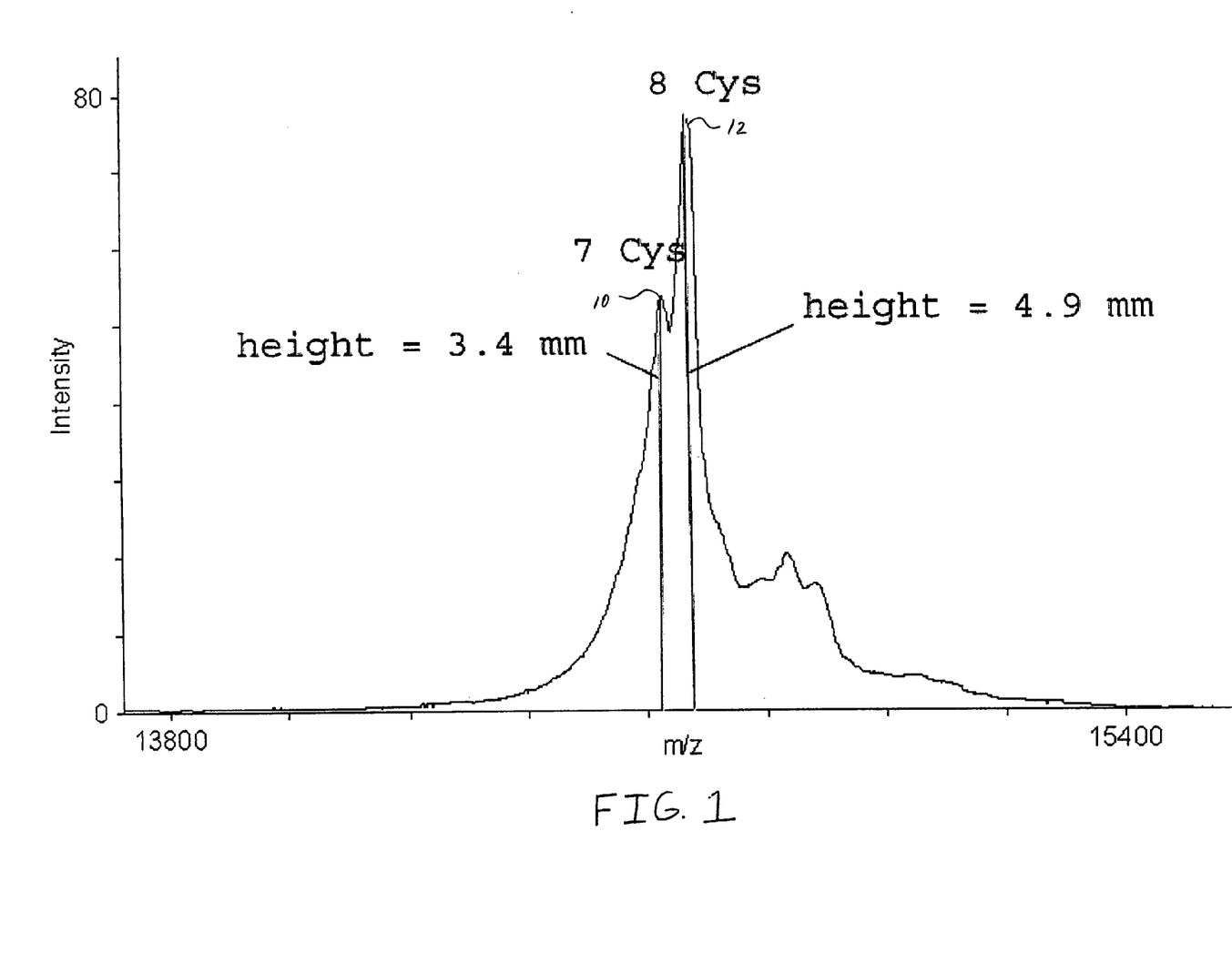
FIG. 1 is a mass spectrum for a sample of lysozyme taken on a MALDI mass spectrometer.

To determine the effectiveness of the reduction alkylation reagent, a MALDI mass spectrometer was used. A mass spectrum for reduced and unreduced lysozyme is shown in FIG. 1. As indicated by reference numeral 10, the mass of unreduced lysozyme is 14,305, the mass of reduced lysozyme is 14,313 and the mass of reduced and alkylated lysozyme is 14,665. Each alkylation adds 44 mass units to the mass of reduced lysozyme. Lysozyme contains 8 cysteines.

To determine the effectiveness of the reagent, the percentage of lysozyme that was reduced and alkylated when subjected to the reagent was determined. To perform this calculation, the height of peak 10 and peak 12 of the mass spectra shown in FIG. 1 was measured. The peak indicated by reference numeral 10 is the point at which 7 cysteine have been alkylyzed and measures 3.4 mm when measured on the correct scale. The peak indicated by reference numeral 12 is the point at which 8 cysteine have been alkylyzed and measures 4.9 mm when measured on the correct scale. The total peak height is then 8.3 mm. The fraction of the peak with 7 alkylated cysteines is determined by dividing the height of the 7 alkylated cysteine peak (10) by the total peak height as shown by equation (1). The fraction of the peak with 7 alkylated cysteines equals 0.41. Referring now to equation (2), the fraction of the peak with 8 alkylated cysteines is the height of the 8 alkylated cysteine peak (12) divided by the total peak height and equals 0.59. The average alkylation value is determined by multiplying the number of alkylated cysteines by the fraction of the peak height for the respective alkylated cysteines as shown in equation (3).

$$\text{Fraction of peak with 7 alkylated cysteine} = 3.4/8.3 = 0.41 \quad (1)$$

$$\text{Fraction of peak with 8 alkylated cysteine} = 4.9/8.3 = 0.59 \quad (2)$$

$$\text{Average alkylation value} = 7(0.41) + 8(0.59) = 7.59 \quad (3)$$

$$\% \text{ reaction} = (7.59/8) * 100 = 94.8\% \quad (4)$$

The average alkylation value is 7.59. The average alkylation value is then divided by the number of alkylated cysteines in lysozyme (8) to determine the percent of lysozyme that has been reduced and alkylated when reacted with the reagent as shown in equation (4).

EXAMPLES

The useful ratio of the reducing agent, the alkylating agent, and the solvent for the reagent were determined by titration. Titration of the triethylphosphine reducing agent was done at concentrations of 0.1, 0.25, 0.5 and 1.0 volume percent. Substantially complete alkylation, as determined by MALDI mass spectrometry analysis, was obtained at concentrations of 0.25 volume percent and higher as will be described in the following examples.

Example 1

A purified lysozyme protein (having a mass of 14299.9 obtained by MALDI MS) in aqueous solution was adjusted to pH 10 with 0.1 M ammonium carbonate. An equal volume of the present reagent comprising 0.5% triethylphosphine, 2% iodoethanol and 97.5% acetonitrile was added to the protein solution. The protein/reagent mixture was capped and incubated at 37° C. for one hour and then uncapped and subjected to a vacuum for about an hour to produce a dried pellet in the container. The dried pellet was reconstituted in the same container to the original volume with a trypsin solution. The reconstituted protein was determined by MALDI MS to have a mass of 14650.9, a difference of 351, which corresponds to the addition of a 44 Da ethanol to each of the eight cysteines in the reduced and alkylated lysozyme.

Example 2

The procedure of Example 1 was repeated with BSA substituted lysozyme. The BSA showed a gain in mass of 1539, which corresponds to a 44 Da alkylation for each of the 35 cysteines in BSA indicating the reduction and alkylation were successful.

Example 3

An unfractionated serum sample was dried under vacuum. The resulting protein pellet was then redissolved in the same container with a volume of 8 M urea, and 0.1 M ammonium carbonate (pH 10) equal to the original volume of the serum sample in order to denature the proteins and maintain their solubility. An equal volume of the present reagent comprising 0.5% triethylphosphine, 2% iodoethanol and 97.5% acetonitrile was added to the protein solution. The protein/reagent mixture was capped and incubated at 37° C. for one hour and then uncapped and subjected to a vacuum for about an hour to produce a dried pellet in the container. The dried pellet was reconstituted in the same container with five times the original volume of a trypsin solution. The sites of alkylation were verified by subjecting the reconstituted material to LC/MS/MS analysis following incubation with trypsin. Sequence coverage as high as 90% has been observed by mass spectral analysis following trypsin digestion.

Example 4

A portion of an SDS-polyacrylamide gel containing a protein that was stained with Coomassie blue was placed in a container. A volume of the present reagent comprising 0.25% triethylphosphine, 1% iodoethanol, 48.75% acetonitrile, and 50% 0.1 M ammonium carbonate (pH 10) was added to the container holding the gel-encapsulated, stained protein. The container was capped and incubated at 37° C. for one hour and then uncapped and the excess reagent was decanted. The gel piece was dehydrated with a volume of pure acetonitrile equal to the volume of the reagent for five minutes, the acetonitrile was decanted and the gel placed under vacuum for about one hour. The dried gel containing the protein was reconstituted with 5 to 10 µl of a 20 µg/mL solution of trypsin. Following trypsin digestion sequence coverage as high as 60% has been recorded by mass spectral analysis.

Example 5

In some iterations of the above examples, the distinct odor of triethylphosphine was detected in the dried material that remained following vacuuming. Trace amounts (<1 mM) of chelated copper (II) citrate was added to the trypsin solutions to neutralize any remaining triethylphosphine that could potentially break the disulphide bonds in the trypsin.

Example 6

A sample of serum separated from blood was diluted with urea in order to denature the proteins in the serum and to keep them soluble. To the serum sample was added an equal volume of the present reagent comprising 0.5% triethyphosphene, 2% iodoethanol and 97.5% acetonitrile. The reagent/serum mixture was incubated for one hour at 37° C. and subjected to a vacuum for about an hour to produce a dried pellet in the container.

The dried pellet was reconstituted in the same container with 5 fold excess volume of a trypsin solution.

Example 7

A sample of serum was processed as above but without dilution with urea. Similar results were observed.

Example 8

A portion of gel holding a stained protein sample was obtained. It was incubated for an hour at 37° C. in a solution comprising 1 mL of 100 nM ammonium carbonate (pH 10) and 1 mL of a reagent comprising 97.5% acetonitrile, 2% iodoethanol and 0.5% triethylphosphine. The liquid was decanted following incubation and placed under vacuum for an hour to produce a dried pellet.

The pellet was reconstituted in a liquid trypsin solution containing trace amounts of cooper (less than 1 mM) in citrate.

Example 9

Figure 2:
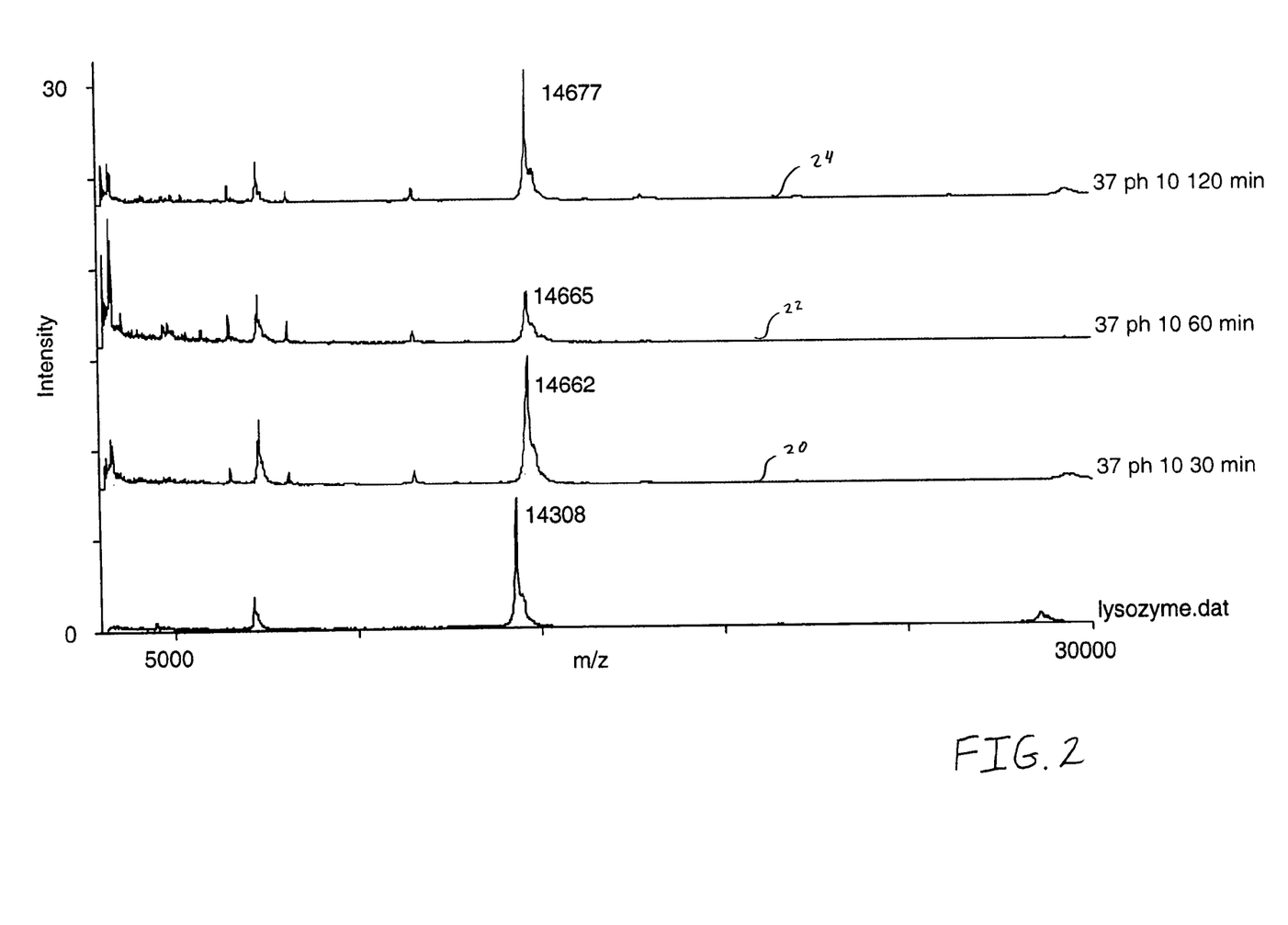
FIG. 2 is a mass spectrum of protein samples after 30 minutes, 60 minutes, and 120 minutes in incubation at 37° C. in a solution having a pH of about 10.

Forty-five microliters of a 1 mg/mL solution of lysozyme in water was placed in a tube. 5 µl of 1 M ammonium carbonate solution having a pH of 11 was added to the tube. The tube then received 50 µl of the alkylation/reduction cocktail which consisted of 97.5% acetonitrile, 2% iodoethanol and 0.5% triethylphosphine. The resulting solution was 50% acetonitrile, 1% iodoethanol and 0.25% triethylphosphine. The final pH of the solution was checked on a micro-pH meter and was found to be about 10. The solution was incubated at 37° C. for 30 minutes, 60 minutes and 120 minutes. At the end of each incubation period, 10 µl of the protein solution was removed and diluted to 100 µl with water and captured on a C4 ZIPTIP. The bound protein was then eluted onto a MALDI target with 1–2 µl of 50% of acetonitrile, 0.05% trifluoroacetic acid after which 1 µl of a saturated solution of sinnapinic acid in 33% acetonitrile, 0.067% trifluoroacetic acid was added to the protein spot. The spot was then allowed to dry and the MALDI target was then loaded in a Voyager Pro mass spectrometer and the mass spectra was acquired in the linear mode. The mass spectra for the protein samples removed at the periods of 30 minutes, 60 minutes and 120 minutes are shown in FIG. 2.

Based on the spectra represented by reference numeral 20 and the calculation method described above, 91% of the lysozyme was reduced and alkylated after 30 minutes of incubation. Based on the spectra represented by reference numeral 22 and the calculation method described above, 95% of the lysozyme was reduced and alkylated after 60 minutes of incubation. Based on the spectra represented by reference numeral 24 and the calculation method described above, 100% of the lysozyme was reduced and alkylated after 120 minutes of incubation.

Example 10

Figure 3:
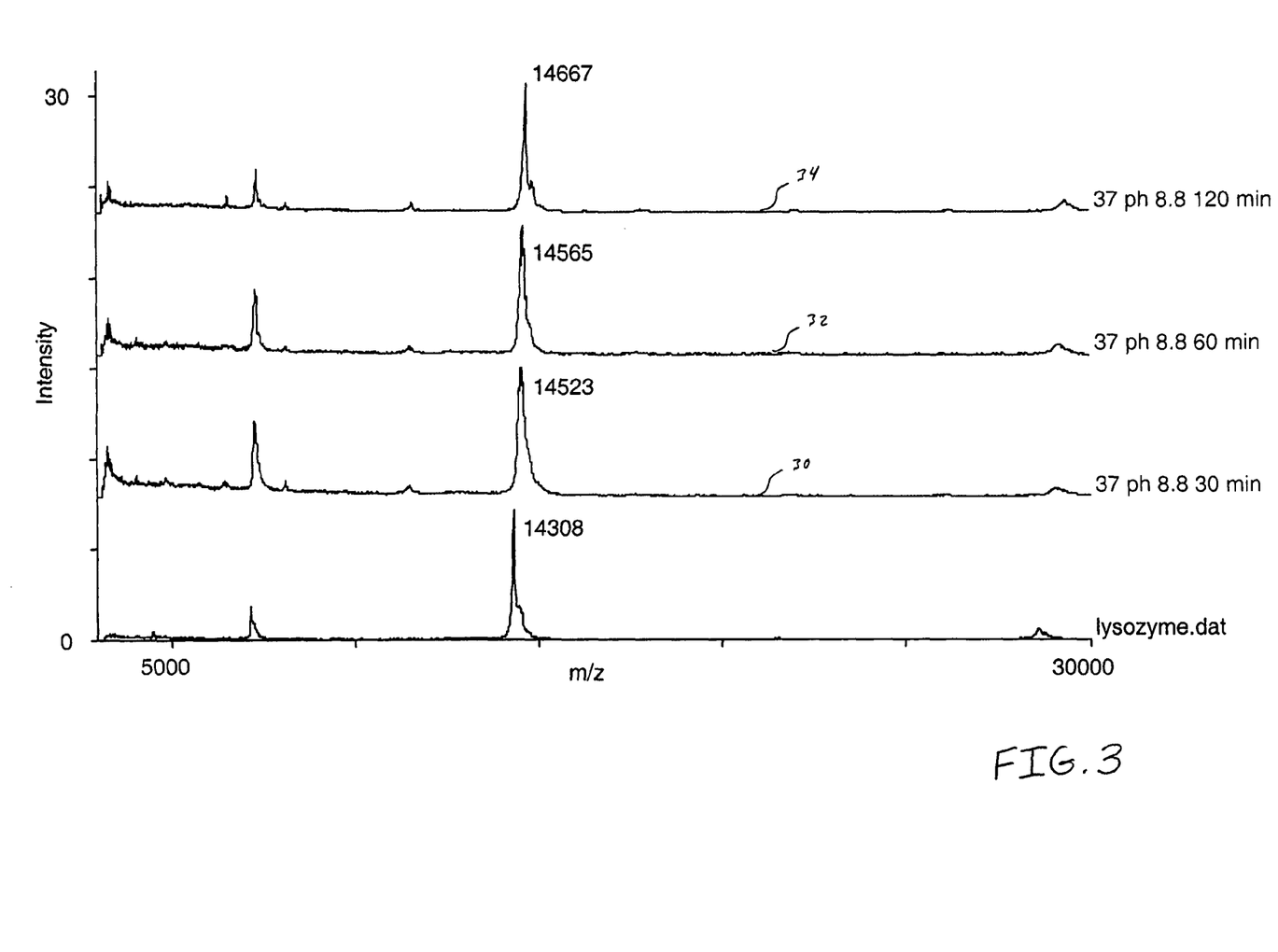
FIG. 3 is a mass spectrum of protein samples after 30 minutes, 60 minutes, and 120 minutes in incubation at 37° C. in a solution having a pH of about 8.8.

Forty-five microliters of a 1 mg/mL solution of lysozyme in water was placed in a tube. 5 μl of 1 M ammonium bicarbonate was added to the tube. Next, the tube received 50 μl of the alkylation/reduction cocktail which consisted of 97.5% acetonitrile, 2% iodoethanol and 0.5% triethylphosphine. The resulting solution was 50% acetonitrile, 1% iodoethanol and 0.25% triethylphosphine. The final pH of the solution was checked on a micro-pH meter and found to be about 8.8. The solution was incubated at 37° C. for time periods of 30 minutes, 60 minutes and 120 minutes. At the end of each incubation period, 10 μl of the protein solution was removed and diluted to 100 μl and captured on a C4 ZIPTIP. The bound protein was eluted onto a MALDI target with 1–2 μl of 50% acetonitrile, 0.05% trifluoroacetic acid after which 1 μl of a saturated solution of sinnapinic acid in 33% acetonitrile, 0.067% trifluoroacetic acid was added to the protein spot. The spot was allowed to dry and the MALDI target was loaded into a Voyager Pro mass spectrometer and the mass spectra acquired in the linear mode. The resulting mass spectra are shown in FIG. 3.

Based upon the calculation method described above and the mass spectra shown by reference numeral 30, 62% of the lysozyme was reduced and alkylated after the 30 minute incubation period. Based upon the calculation method described above and the mass spectra shown by reference numeral 32, 78% of the lysozyme was reduced and alkylated after the 60 minute incubation period. Based upon the calculation method described above and the mass spectra shown by reference numeral 34, 96% of the lysozyme was reduced and alkylated after the 120 minute incubation period.

Example 11

Figure 4:
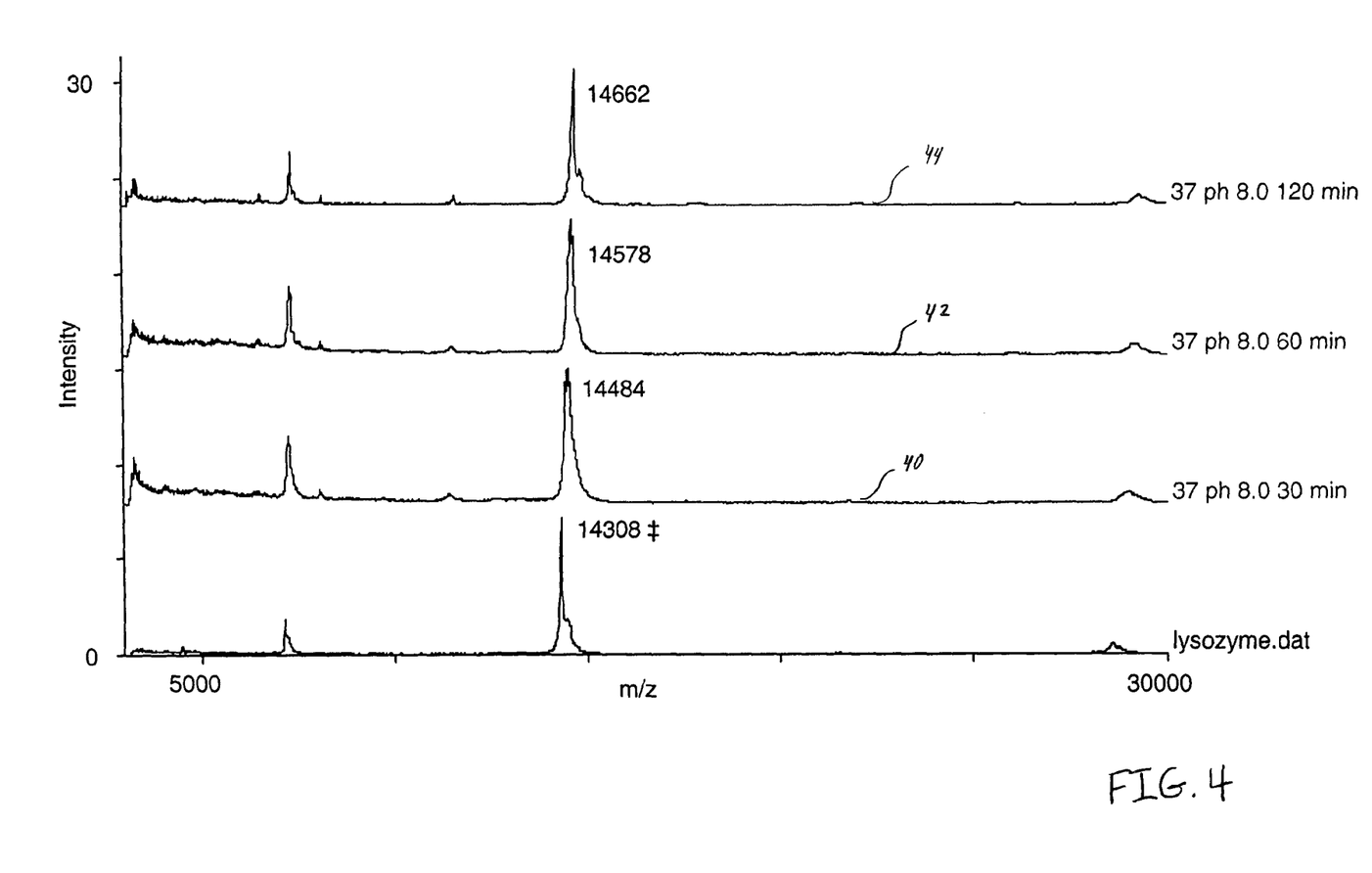
FIG. 4 is a mass spectrum of protein samples after 30 minutes, 60 minutes, and 120 minutes in incubation at 37° C. in a solution having a pH of about 8.

Forty-five microliters of a 1 mg/mL solution of lysozyme in water was placed in a tube. Next, 5 μl of 1 M ammonium bicarbonate was added to the tube and the pH of the solution was adjusted by adding small volumes of 10% formic acid until the final pH of the solution was about 8.0. The final pH of the solution was checked on a micro-pH meter. The tube then received 50 μl of the alkylation/reduction cocktail which consisted of 97.5% acetonitrile, 2% iodoethanol and 0.5% triethylphosphine. The solution was incubated at 37° C. for time periods of 30 minutes, 60 minutes and 120 minutes. At the end of each incubation period, 10 μl of the protein solution was removed and diluted to 100 μl and captured on a C4 ZIPTIP. The bound protein was eluted onto a MALDI target with 1–2 μl of 50% acetonitrile, 0.05% trifluoroacetic acid after which 1 μl of a saturated solution of sinnapinic acid in 33% acetonitrile, 0.067% trifluoroacetic acid was added to the protein spot. The spot was allowed to dry and the MALDI target was loaded into a Voyager Pro mass spectrometer and the mass spectra acquired in the linear mode. The resulting mass spectra are shown in FIG. 4.

Based upon the calculation method described above and the mass spectra indicated by reference numeral 40, 42% of the lysozyme in the solution was reduced and alkylated in the 30 minute incubation period. Based upon the calculation method described above and the mass spectra indicated by reference numeral 42, 79% of the lysozyme in the solution was reduced and alkylated in the 60 minute incubation period. Based upon the calculation method described above and the mass spectra indicated by reference numeral 44, 95% of the lysozyme in the solution was reduced and alkylated in the 120 minute incubation period.

Example 12

Forty-five microliters of a 1 mg/mL solution of lysozyme in water was placed in a tube. 5 μl of 1 M ammonium carbonate solution having a pH of 11 was added to the tube. The tube then received 50 μl of the alkylation/reduction cocktail which consisted of 97.5% acetonitrile, 2% iodoethanol and 0.5% triethylphosphine. The final pH of the solution was checked on a micro-pH meter and found to be about 10. The solution was incubated at room temperature (approximately 23° C.) for 120 minutes. At the end of the incubation period, 10 μl of the protein solution was removed and diluted to 100 μl of water and captured on a C4 ZIPTIP. The bound protein was eluted onto a MALDI target with 1–2 μl of 50% acetonitrile, 0.05% trifluoroacetic acid after which 1 μl of a saturated solution of sinnapinic acid in 33% acetonitrile, 0.067% trifluoroacetic acid was added to the protein spot. The spot was allowed to dry and the MALDI target was loaded into a Voyager Pro mass spectrometer and the mass spectra acquired in the linear mode. The resulting mass spectra are shown in FIG. 4.

Figure 5:
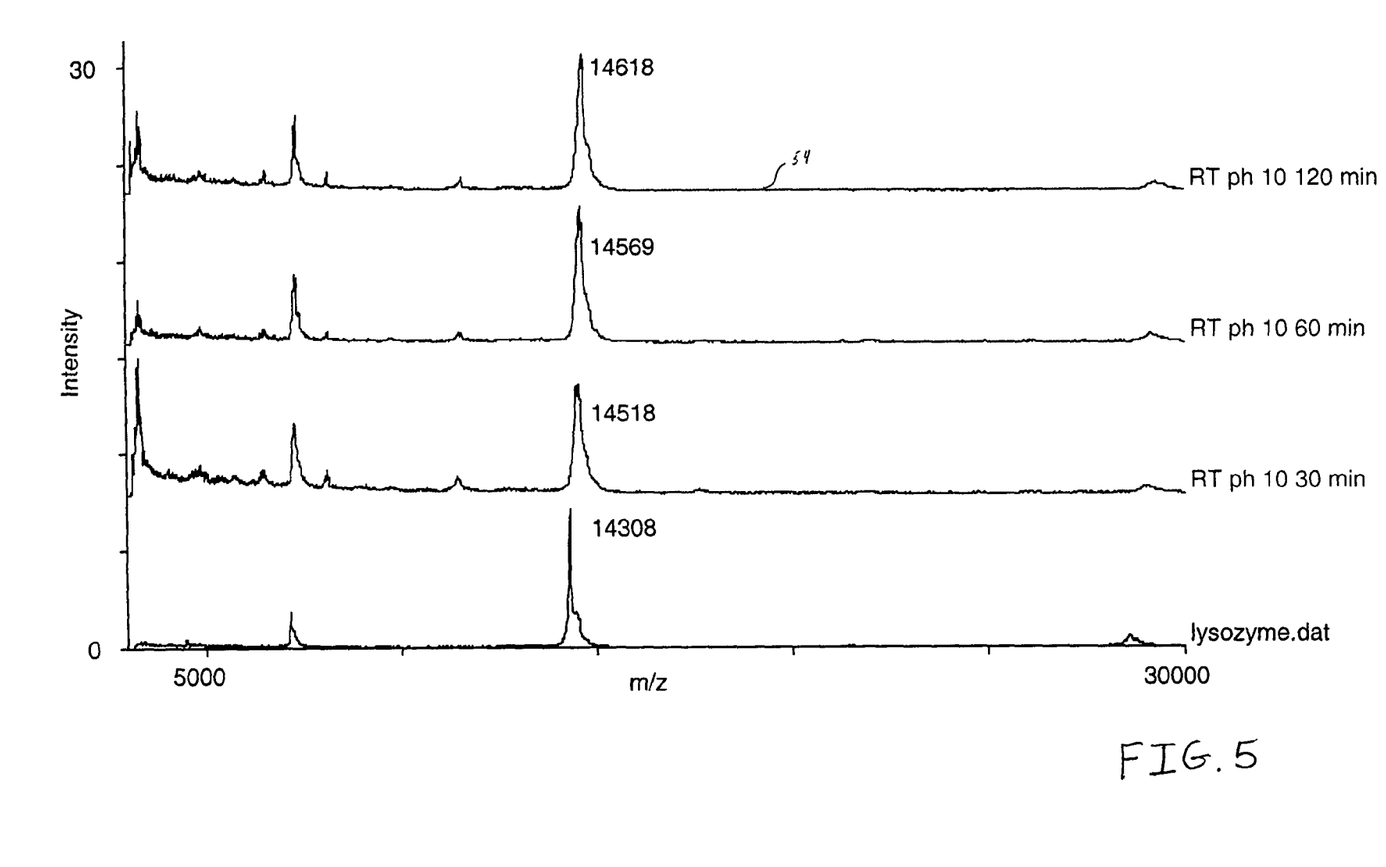
FIG. 5 is a mass spectrum of protein samples after 30 minutes, 60 minutes, and 120 minutes in incubation at room temperature in a solution having a pH of about 10.

Based upon the calculation method described above and the mass spectra illustrated by reference numeral 54, 88% of the lysozyme in the protein solution was reduced and alkylated in the 120 minute incubation period.

Example 13

Figure 6:
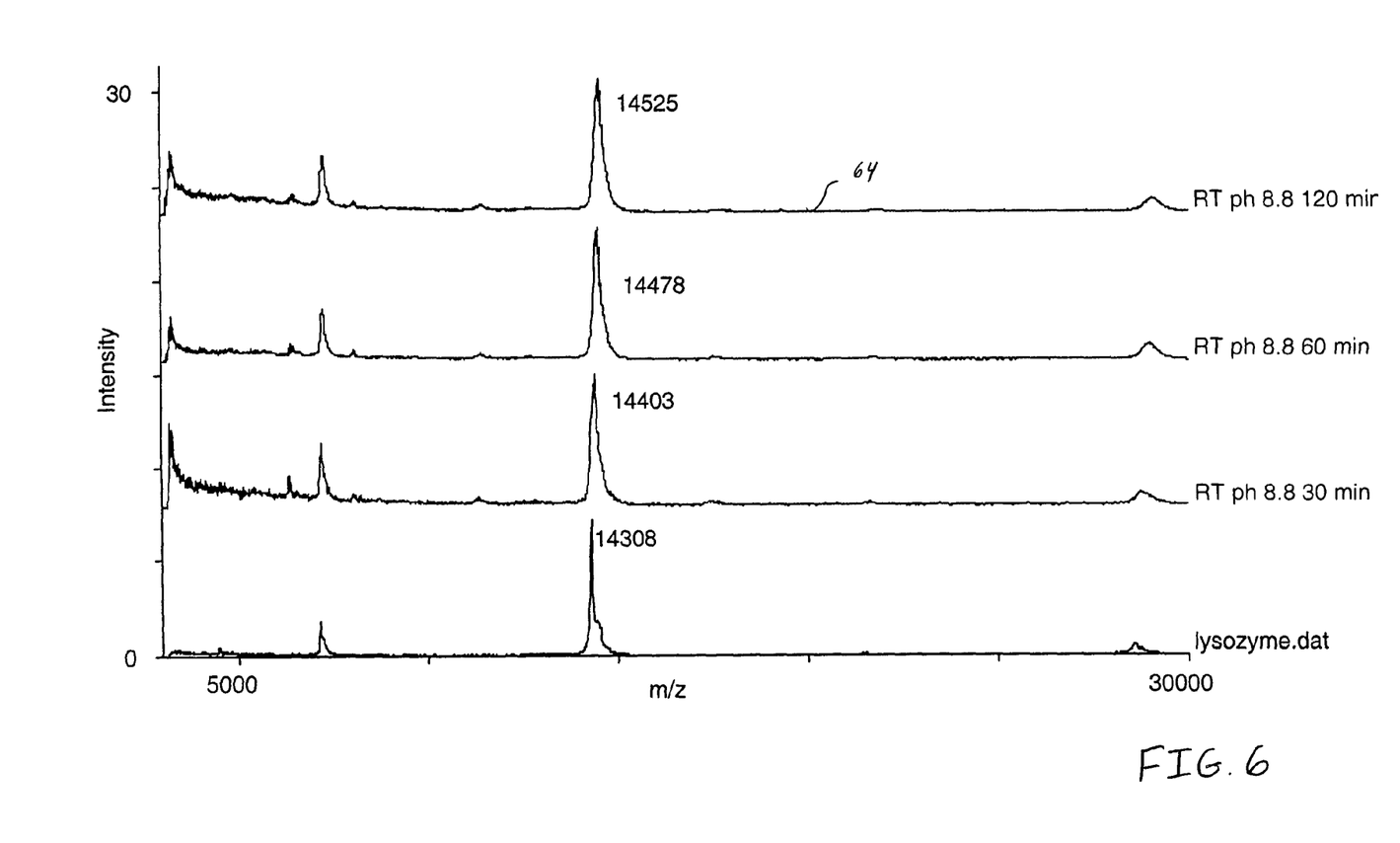
FIG. 6 is a mass spectrum of protein samples after 30 minutes, 60 minutes, and 120 minutes in incubation at room temperature in a solution having a pH of about 8.8.

Example 13 was identical to Example 12, except that 5 μl of 1 M ammonium bicarbonate was added to the original lysozyme in water solution rather than 5 μl of 1 M ammonium carbonate. The final pH of the solution was found to be about 8.8. All incubation periods and testing methods were identical. Based upon the calculation method described above and the mass spectra indicated by reference numeral 64 as shown on FIG. 6, 60% of the lysozyme in the original protein solution was reduced and alkylated in the 120 minute time period.

Example 14

Figure 7:
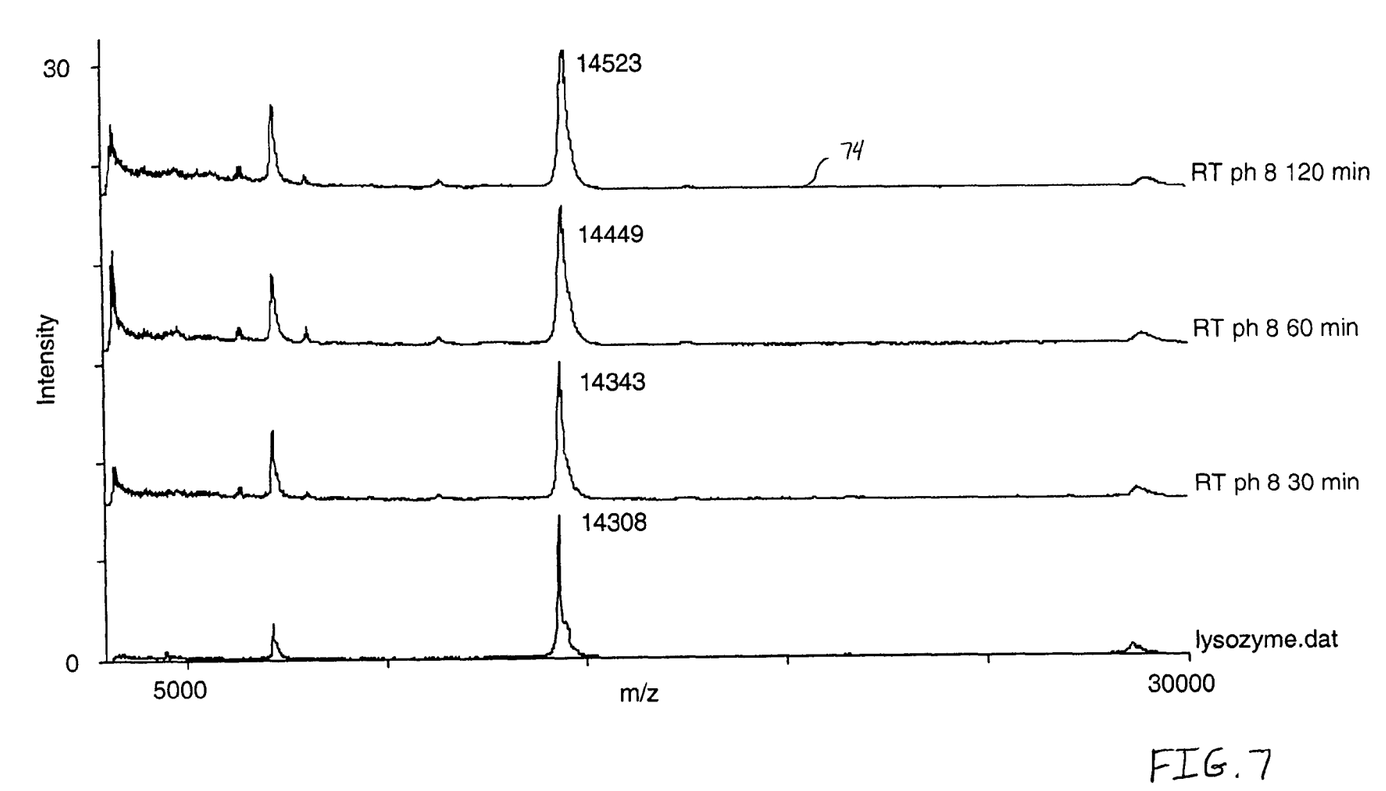
FIG. 7 is a mass spectrum of protein samples after 30 minutes, 60 minutes, and 120 minutes in incubation at room temperature in a solution having a pH of about 8.

Example 14 was identical to Example 13, except that the pH of the original solution was adjusted with small volumes of formic acid until the final pH of the solution was about 8.0. All incubation periods and testing methods were identical. The resulting mass spectra are shown in FIG. 7. Based upon the calculation method described above and the mass spectra indicated by reference numeral 74, 60% of the lysozyme in the original protein solution was reduced and alkylated in the 120 minute incubation period.

Example 15

Figure 8:
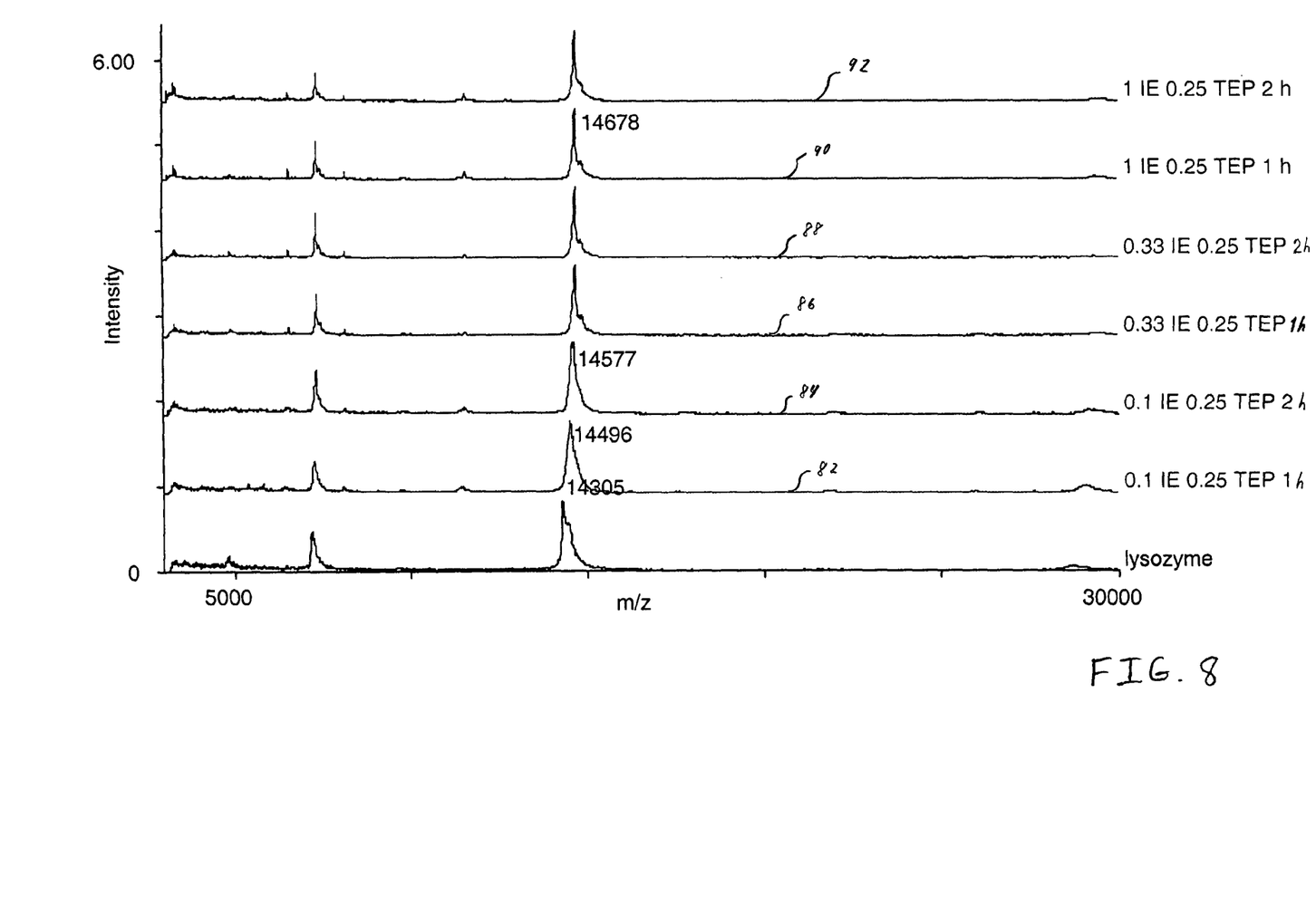
FIG. 8 is a mass spectrum of protein samples taken at time periods of 60 minutes and 120 minutes after incubation while varying the concentration of iodoethanol.

Forty-five microliters of a 1 mg/mL solution of lysozyme in water was placed in a tube with 5 µl of 1 M ammonium carbonate at a pH of 11. The tube then received 50 µl of the alkylation/reduction cocktail which consisted of 97.5% acetonitrile, 2% iodoethanol and 0.5% triethylphosphine. The final pH of the solution was checked on a micro-pH meter and was found to be about 10. The solution was then incubated at 37° C. for time periods of 60 minutes and 120 minutes. At the end of each incubation period, 10 µl of the protein solution was removed and diluted to 100 µl with water and captured on a C4 ZIPTIP. The bound protein was then eluted onto a MALDI target with 1–2 µl of a 50% acetonitrile, 0.05% trifluoroacetic acid after which 1 µl of a saturated solution of sinnapinic acid in 33% acetonitrile, 0.067% trifluoroacetic acid was added to the protein spot. The spot was allowed to dry, then the MALDI target was loaded into a Voyager Pro mass spectra meter and a mass spectra acquired in the linear mode. The resulting mass spectra are indicated by reference numerals 82, 84 as shown in FIG. 8.

Based upon the calculation method described above and the mass spectra indicated by reference numeral 90, 100% of the lysozyme in the original protein solution was reduced and alkylated during the 60 minute incubation period. Based upon the calculation method described above and the mass spectra indicated by reference numeral 92 as shown in FIG. 8, 100% of the lysozyme in the original protein solution was reduced and alkylated during the 120 minute incubation period.

Example 16

Example 16 is identical to Example 15, except the concentration of iodoethanol in the alkylation/reduction cocktail was modified. For this example, the concentration of iodoethanol in the 50 µl solution was 0.66% iodoethanol. The resulting mass spectra are shown by reference numerals 86, 88 on FIG. 8.

Based upon the calculation method described above and the mass spectra indicated by reference numeral 86 as shown in FIG. 8, 95% of the lysozyme in the original protein solution was reduced and alkylated during the 60 minute incubation period. Based upon the calculation method described above and the mass spectra indicated by reference numeral 88 as shown in FIG. 8, 95.4% of the lysozyme in the original protein solution was reduced and alkylated during the 120 minute incubation period.

Example 17

Example 17 is identical to Example 15, except the concentration of iodoethanol in the alkylation/reduction cocktail was modified. For this example, the concentration of iodoethanol in the 50 µl solution of 0.2% iodoethanol. The resulting mass spectra are shown by reference numerals 82, 84 on FIG. 8.

Based upon the calculation method described above and the mass spectra indicated by reference numeral 82 as shown in FIG. 8, 56% of the lysozyme in the original protein solution was reduced and alkylated during the 60 minute incubation period. Based upon the calculation method described above and the mass spectra indicated by reference numeral 84 as shown in FIG. 8, 73% of the lysozyme in the original protein solution was reduced and alkylated during the 120 minute incubation period.

Example 18

Figure 9:
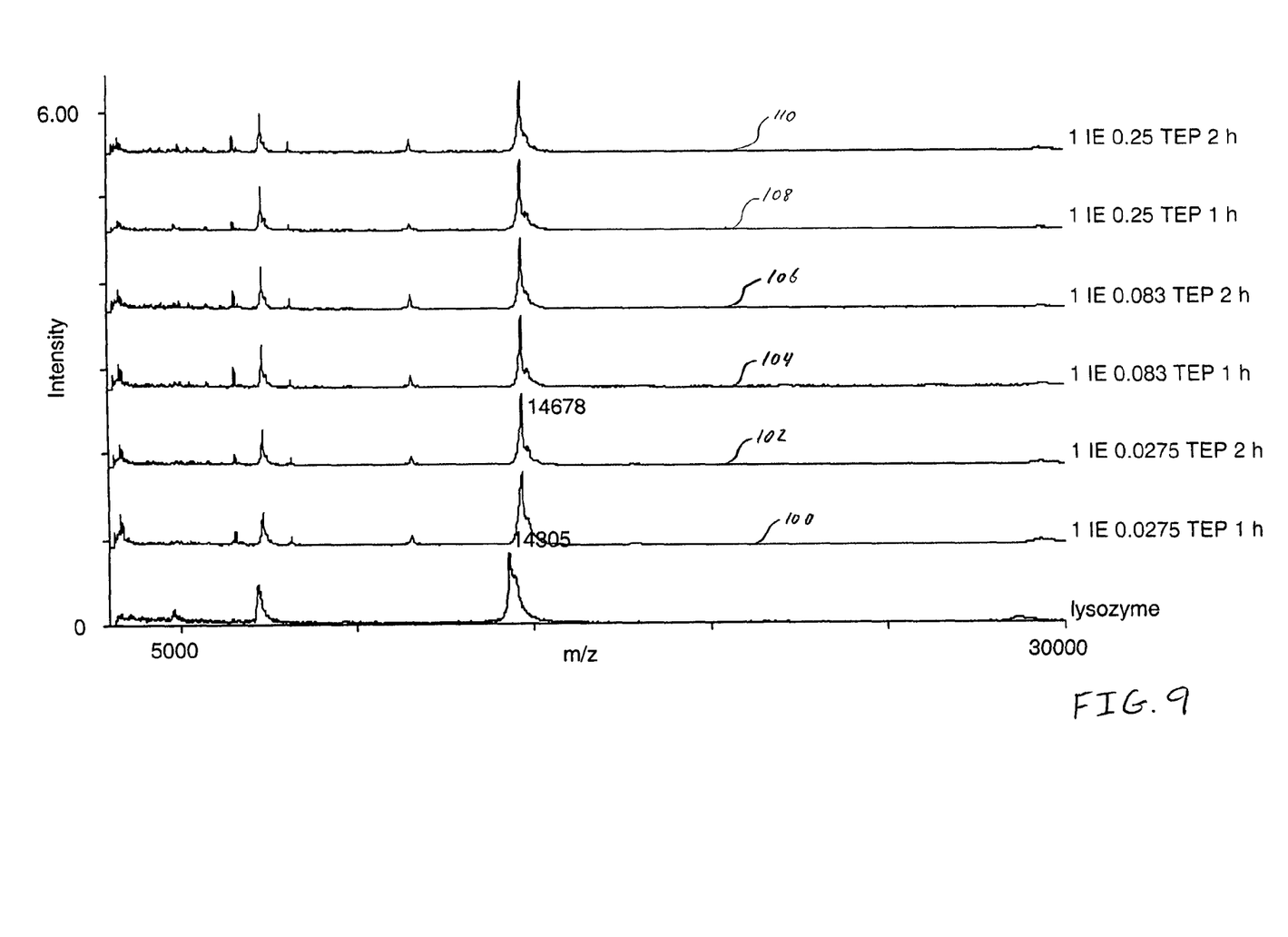
FIG. 9 is a mass spectrum of protein samples taken at time periods of 60 minutes and 120 minutes after incubation while varying the concentration of triethylphosphine.

Forty-five microliters of a 1 mg/mL solution of lysozyme in water was placed in a tube with 5 µl of 1 M ammonium carbonate having a pH of 11. The tube then received 50 µl of the alkylation/reduction cocktail which consisted 97.5% acetonitrile, 2% iodoethanol and 0.5% triethylphosphine. The final pH of this solution was checked with a micro-pH meter and found to be about 10. The solution was then incubated at 37° C. for time periods of 60 minutes and 120 minutes. At the end of each incubation period, 10 µl of the protein solution was removed and diluted to 100 µl with water and captured on a C4 ZIPTIP. The bound protein was eluted onto a MALDI target with 1–2µl of a 50% acetonitrile, 0.05% trifluoroacetic acid after which 1 µl of a saturated solution of sinnapinic acid in 33% acetonitrile, 0.067% trifluoroacetic acid was added to the protein spot. The spot was allowed to dry, then the MALDI target was loaded into a Voyager Pro mass spectra meter and the mass spectra acquired in the linear mode. The resulting mass spectra as shown in FIG. 9.

Based on the calculation method described above and the mass spectra indicated by reference numeral 108, 100% of the lysozyme in the original protein solution was reduced and alkylated in the 60 minute incubation period. Based on the calculation method described above and the mass spectra indicated by reference numeral 110, 100% of the lysozyme in the original protein solution was reduced and alkylated in the 120 minute incubation period.

Example 19

Example 19 is identical to Example 18, except the concentration of the triethylphosphine in the 50 µl alkylation/reduction cocktail was 0.166%, instead of 0.5% as in Example 18. The resulting mass spectra are indicated by reference numerals 104, 106 as shown in FIG. 9.

Based on the calculation method described above and the mass spectra indicated by reference numeral 104, 96% of the lysozyme in the original protein solution was reduced and alkylated in the 60 minute incubation period. Based on the calculation method described above and the mass spectra indicated by reference numeral 106, 100% of the lysozyme in the original protein solution was reduced and alkylated in the 120 minute incubation period.

Example 20

Example 20 is identical to Example 18, except the concentration of the triethylphosphine and the 50 µl alkylation/reduction cocktail was 0.055%, instead of 0.5% as in Example 18. The resulting mass spectra are indicated by reference numerals 100, 102 as shown in FIG. 9.

Based on the calculation method described above and the mass spectra indicated by reference numeral 100, 89.8% of the lysozyme in the original protein solution was reduced and alkylated in the 60 minute incubation period. Based on the calculation method described above and the mass spectra indicated by reference numeral 102, 96.5% of the lysozyme in the original protein solution was reduced and alkylated in the 120 minute incubation period.

Example 21

Forty-five microliters of a 1 mg/mL solution of lysozyme in water was placed in a tube with 5 µl of 2 M methylamine (in methanol). The tube then received 50 µl of alkylation/reduction cocktail which consisted of 97.5% acetonitrile, 2% iodoethanol and 0.5% triethylphosphine. The final pH of the solution was checked on a micro-pH meter and found to be about 11.8. The solution was incubated at 37° C. for 30 minutes. At the end of the incubation period, 10 µl of the protein solution was removed and diluted to 100 µl with water and captured of a C4 ZIPTIP. The bound protein was eluted onto a MALDI target with 1–2 µl of a 50% acetonitrile, 0.05% trifluoroacetic acid after which 1 µl of a saturated solution of sinnapinic acid in 33% acetonitrile, 0.067% trifluoroacetic acid was added to the protein spot. The spot was allowed to dry, then the MALDI target was loaded into a Voyager Pro mass spectra meter and the mass spectra acquired in the linear mode. The resulting mass spectra is indicated by reference numeral 120 on FIG. 10.

Figure 10:
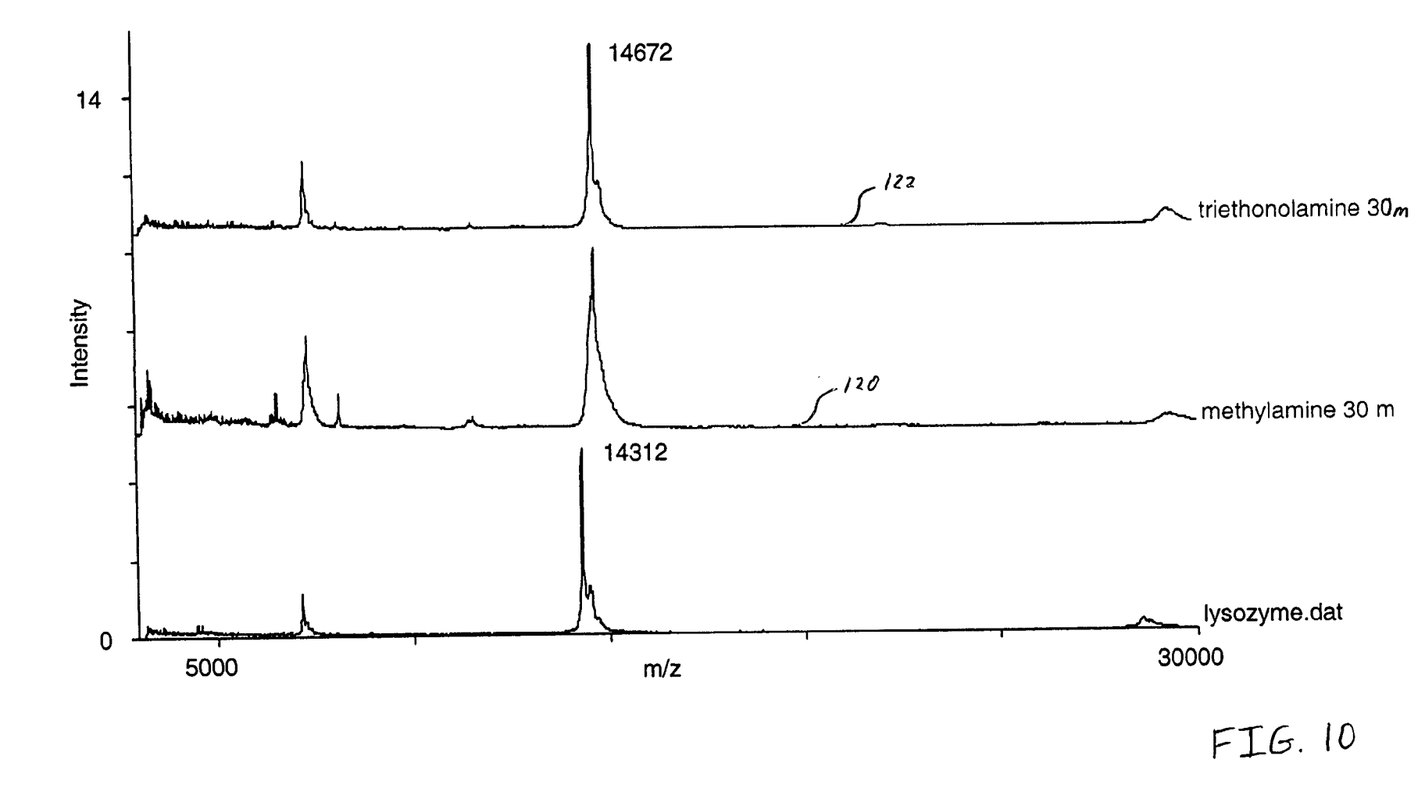
FIG. 10 is a mass spectrum of protein samples that have been reduced and alkylated using a methylamine reagent and a triethanolamine reagent and subjected to a 30 minute incubation period.

Based upon the calculation method described above and the mass spectra indicated by reference numeral 120 as shown in FIG. 10, 100% of the lysozyme in the original protein solution was reduced and alkylated during the 30 minute incubation period.

Example 22

Example 22 is identical to Example 21 except 1 µl of triethanolamine was used instead of the 2 M methylamine. The final pH of the solution was checked on a micro-pH meter and found to be about 11.4. The resulting mass spectra is indicated by reference numeral 122 on FIG. 10.

Based upon the calculation method described above and the mass spectra indicated by reference numeral 122 as shown in FIG. 10, about 95% of the lysozyme in the original protein solution was reduced and alkylated during the 30 minute incubation period.

The foregoing description of the invention is illustrative only, and is not intended to limit the scope of the invention to the precise terms set forth. Although the invention has been described in detail with reference to certain illustrative embodiments, variations and modifications exist within the scope and spirit of the invention as described and defined in the following claims.

What is claimed is:

1. A composition configured to modify a protein having disulfide bonds, the composition comprising:
    a volatile reagent for breaking the disulfide bonds in the protein and preventing reformation thereof, the volatile reagent including a volatile solvent; and
    a water soluble alkylating agent;
    wherein the protein remains substantially dissolved in the composition at solvent compositions of about 50% water.

2. The composition of claim 1, wherein the volatile solvent includes acetonitrile.

3. The composition of claim 1, wherein the alkylating agent is selected from the group consisting of iodoethanol, bromoethanol, iodopropanol, bromopropanol, iodomethanol, bromomethanol and mixtures thereof.

4. The composition of claim 1, wherein the concentration of the alkylating agent is between about 0.1% to about 1.0% by volume, based on a total volume of the composition.

5. The composition of claim 1, wherein the volatile reagent further includes a reducing agent.

6. The composition of claim 5, wherein the reducing agent is selected from the group consisting of triethylphosphine, trimethylphosphine, tripropylphosphine, tributylphosphine and mixtures thereof.

7. The composition of claim 5 wherein the solvent is selected from the group consisting of water, acetonitrile and mixtures thereof.

8. The composition of claim 1, wherein the volatile reagent includes a reducing agent selected from the group consisting of triethylphosphine, trimethylphosphene, tripropylphosphine, tributyiphosphine and mixtures thereof.

9. The composition of claim 8, wherein the concentration of the reducing agent is between about 0.025% to about 0.25% by volume, based on a total volume of the composition.

10. The composition of claim 8, wherein the alkylating agent is selected from the group consisting of iodoethanol, bromoethanol, iodopropanol, bromopropanol, iodomethanol, bromomethanol and mixtures thereof.

11. The composition of claim 10, wherein the volatile solvent is selected from the group consisting of water, acetonitrile and mixtures thereof.

12. The composition of claim 1, wherein the volatile solvent is up to 50% water by volume, based on the total volume of the composition.

13. The composition of claim 1, wherein the volatile reagent includes a buffer configured to buffer the pH of the composition to about pH 10.

14. The composition of claim 13, wherein the buffer is 0.1M ammonium carbonate.

15. A kit for one-step reduction and alkylation of a protein sample, the kit including:
    a substantially volatile reducing agent to reduce the protein sample;
    a substantially volatile alkylating agent to alkylate the protein sample, the alkylating agent being water soluble;
    a substantially volatile solvent to substantially dissolve the protein sample; and
    wherein the protein remains substantially dissolved in a composition containing the reducing agent, the alkylating agent and the solvent at solvent compositions of about 50% water.

16. The kit of claim 15, wherein the volatile reducing agent is selected from the group consisting of triethyiphosphine, trimethyl phosphine, tripropyl phosphine, tributylphosphine and mixtures thereof.

17. The kit of claim 16, wherein the reducing agent has a concentration of 0.025% to about 0.25% by volume, based on a total volume of the reducing agent, the alkylating agent, and the solvent.

18. The kit of claim 15, wherein the volatile alkylating agent is selected from the group consisting of iodoethanol, bromoethanol, iodopropanol, bromopropanol, iodomethanol, bromomethanol and mixtures thereof.

19. The kit of claim 18, wherein the alkylating agent has a concentration of 1.0% by volume, based on a total volume of the reducing agent, the alkylating agent, and the solvent.

20. The kit of claim 15, wherein the volatile, solvent is selected from the group consisting of water, acetonitrile and mixtures thereof.

21. The kit of claim 20, wherein the solvent has a concentration of 50% by volume, based on a total volume of the reducing agent, the alkylating agent, and the solvent.

22. The kit of claim 15, wherein the alkylating agent has a concentration of 1.0% by volume, based on a total volume of the reducing agent, the alkylating agent, and the solvent.

23. The kit of claim 15, wherein the reducing agent has a concentration of 0.25% by volume, based on a total volume of the reducing agent, the alkylating agent, and the solvent.

24. The kit of claim 15, wherein the solvent has a concentration of 50% by volume, based on a total volume of the reducing agent, the alkylating agent, and the solvent.

25. The kit of claim 15, further including a buffer configured to buffer the reducing agent, alkylating agent, and the solvent to a pH of about 10.

26. The kit of claim 25, wherein the buffer is ammonium carbonate.

27. The kit of claim 15, wherein the alkylating agent, the reducing agent, and the solvent are combined with the protein sample in a single container.

28. A composition configured to modify proteins having disulfide bonds, the composition comprising:
   a single volatile reagent for breaking the disulfide bonds and preventing reformation thereof;
   the volatile reagent including an alkylating agent selected from the group consisting of iodoethanol, bromoethanol, iodopropanol, bromopropanol, iodomethanol, bromomethanol and mixtures thereof.

29. The composition of claim 28, wherein the concentration of the alkylating agent is between about 0.1% to about 1.0% by volume, based on a total volume of the composition.

30. The composition of claim 29, wherein the volatile reagent further includes a reducing agent.

31. The composition of claim 30, wherein the reducing agent is selected from the group consisting of triethylphosphine, trimethylphosphine, tripropylphosphine, tributylphosphine and mixtures thereof.

32. The composition of claim 28, wherein the volatile reagent includes a volatile solvent.

33. The composition of claim 32, wherein the volatile solvent comprises water.

34. The composition of claim 32, wherein the volatile solvent consists essentially of water, acetonitrile and mixtures thereof.

35. The composition of claim 32, wherein the volatile solvent is about 50% water by volume.

36. The composition of claim 28, wherein the volatile reagent includes a buffer.

37. A kit for one-step reduction and alkylation of a protein sample, the kit including:
   a substantially volatile reducing agent to reduce the protein sample;
   a substantially volatile alkylating agent to alkylate the protein sample, the alkylating agent selected from the group consisting of iodoethanol, bromoethanol, iodopropanol, bromopropanol, iodomethanol, bromomethanol and mixtures thereof; and
   a substantially volatile solvent to substantially dissolve the protein sample.

38. The kit of claim 37, wherein the volatile reducing agent is selected from the group consisting of triethylphosphine, trimethylphosphine, tripropylphosphine, tributylphosphine and mixtures thereof.

39. The kit of claim 38, wherein the reducing agent has a concentration of 0.025% to about 0.25% by volume, based on a total volume of the reducing agent, the alkylating agent, and the solvent.

40. The kit of claim 37, wherein the alkylating agent has a concentration of 1.0% by volume, based on a total volume of the reducing agent, the alkylating agent, and the solvent.

41. The kit of claim 37, wherein the volatile solvent comprises water.

42. The kit of claim 41, wherein the solvent has a concentration of about 50% water by volume, based on a total volume of the reducing agent, the alkylating agent, and the solvent.

43. The kit of claim 37, wherein the alkylating agent has a concentration of about 1.0% by volume, based on a total volume of the reducing agent, the alkylating agent, and the solvent.

44. The kit of claim 37, further including a buffer configured to buffer the reducing agent.

45. A composition configured to modify proteins having disulfide bonds, the composition comprising:
   a volatile reagent for breaking the disulfide bonds and preventing reformation thereof;
   the volatile reagent including a reducing agent selected from the group consisting of triethylphosphine, trimethylphosphene, tripropylphosphine, tributylphosphine and mixtures thereof; and
   the volatile reagent including an alkylating agent selected from the group consisting of idoethanol, bromoethanol, iodopropanol, bromopropanol, iodomethanol, and mixtures thereof.

* * * * *